United States Patent [19]

Hara et al.

[11] Patent Number: 5,149,877
[45] Date of Patent: * Sep. 22, 1992

[54] PROCESS FOR PRODUCING ALKYLENAMINE

[75] Inventors: Yasushi Hara, Shin-nanyo; Yukio Ito, Kudamatsu; Kazuhiko Sekizawa, Shin-nanyo, all of Japan

[73] Assignee: Tosoh Corporation, Yamaguchi, Japan

[*] Notice: The portion of the term of this patent subsequent to Dec. 17, 2008 has been disclaimed.

[21] Appl. No.: 530,431

[22] Filed: Jun. 1, 1990

Related U.S. Application Data

[63] Continuation of Ser. No. 283,975, Dec. 13, 1988, abandoned.

[30] Foreign Application Priority Data

Dec. 18, 1987 [JP] Japan .................................. 62-318913
Dec. 18, 1987 [JP] Japan .................................. 62-318914
Dec. 18, 1987 [JP] Japan .................................. 62-318915

[51] Int. Cl.$^5$ ............................................. C07C 209/14
[52] U.S. Cl. ........................................ 564/479; 502/353
[58] Field of Search ........................ 564/479; 502/353

[56] References Cited

U.S. PATENT DOCUMENTS

| 4,376,732 | 3/1983 | Ramirez ............................ 564/463 |
| 4,841,061 | 6/1989 | Shimasaki et al. .................. 546/184 |
| 4,906,782 | 3/1990 | Hara et al. ........................... 564/478 |
| 5,011,999 | 4/1991 | Bowman et al. ..................... 564/479 |

FOREIGN PATENT DOCUMENTS

| 0256516 | 2/1988 | European Pat. Off. ............ 502/353 |
| 3543228 | 6/1986 | Fed. Rep. of Germany ....... 564/479 |
| 3068539 | 3/1988 | Japan ................................. 502/353 |

OTHER PUBLICATIONS

Barnes et al., "Ethylenediamine by Low-Pressure Ammonolysis of Monethanolamine", Ind. Eng. Chem. Prod. Res. Dev., 1981, vol. 20, pp. 399–407.

Primary Examiner—Richard L. Raymond
Assistant Examiner—Scott C. Rand
Attorney, Agent, or Firm—Nixon & Vanderhye

[57] ABSTRACT

A process for producing an alkylenamine, which comprises reacting ammonia and/or an alkylenamine with an alkanolamine in the presence of niobium oxide treated with an acid, to obtain an alkylenamine having an increased number of alkylene chains over the ammonia and/or the alkylenamine as starting material.

4 Claims, No Drawings

PROCESS FOR PRODUCING ALKYLENAMINE

This is a continuation of application Ser. No. 07/283,975, filed Dec. 13, 1988, now abandoned.

BACKGROUND OF THE INVENTION

1. Field of the Invention

The present invention relates to a process for producing an alkylenamine. More particularly, it relates to a process for producing an alkylenamine using, as a catalyst, niobium oxide treated with an acid.

2. Discussion of Background

As a process for producing alkylenamines, particularly ethylenamines which are particularly important from the industrial point of view, it is known to react ethylene dichloride with ammonia. By this process, the production of piperazine and piperazine ring-containing cyclic ethylenamines is small. Namely, it is possible to obtain ethylenamines having high noncyclic rates and industrially preferred quality. This process is practically widely used. However, it has a problem that a large amount of sodium chloride is formed as a by-product, and its separation and treatment are costly.

Another process is also widely practically employed wherein a monoethanolamine is used as starting material, and ammonia is reacted thereto in the presence of hydrogen and a hydrogenation catalyst to obtain an ethylenamine. However, according to this process, piperazine ring-containing cyclic ethylenamines which are undesirable from the viewpoint of quality, are likely to be produced in a substantial amount although ethylenediamines may be produced with high efficiency. Therefore, it is difficult to produce polyethylenepolyamines having high molecular weights.

In addition to these processes, a process has been proposed wherein monoethanolamine is used as starting material, and ammonia or/and ethylenamine are reacted thereto by using a phosphorus-containing substance as catalyst to produce an ethylenamine. For example, Japanese Unexamined Patent Publication No. 147600/1976 discloses a process wherein phosphoric acid or phosphorous acid is used as catalyst. However, these catalysts are soluble in the reaction solution containing water. Therefore, a special step for the separation and recovery from the reaction solution is required. Japanese Unexamined Patent Publication No. 87424/1982 discloses a process wherein a sulfur-containing substance such as sulfuric acid or ammonium sulfate is used as catalyst. However, these catalysts are also soluble in the reaction solution containing water, and thus, a special step for the separation and recovery from the reaction solution is likewise required.

Under the circumstances, processes for the production of ethylenamines have been proposed wherein various salts of phosphoric acid and supported phosphoric acid insoluble in the reaction solution containing water are used as catalysts. U.S. Pat. No. 4,448,997 discloses a process for producing ethylenamines wherein aluminum phosphate is used as catalyst, and Japanese Unexamined Patent Publication No. 41641/1985 discloses such a process wherein a phosphate of a metal of Group IIIb such as lanthanum phosphate is used as catalyst. Further, Japanese Unexamined Patent Publication No. 150538/1984 discloses a process wherein phosphoric acid supported on e.g. titanium dioxide is used as catalyst. However, these phosphates and supported phosphoric acid are substantially poorer in the catalytic activities than free phosphoric acid. Further, by the use of these phosphoric acid type catalysts, it is not possible to reduce piperazine ring-containing cyclic amines undesirable from the viewpoint of quality to a level sufficiently low for the industrial purpose. Further, Japanese Unexamined Patent Publication No. 78945/1985 discloses a process wherein niobium phosphate is used as catalyst. However, with this catalyst, it is not possible to reduce piperadine ring-containing cyclic amines undesirable from the viewpoint of quality to a level sufficiently low for the industrial purpose. As a phosphorus-containing catalyst having high activities, there is a phosphorus-containing ion exchange resin. However, this catalyst is poor in the heat resistance and thus has a problem in the catalytically useful life.

As a non-phosphorus catalyst, silica or alumina is disclosed in Japanese Unexamined Patent Publication No. 38329/1980, but the catalytic activities of this catalyst are very low.

As described above, many processes have been disclosed for the production of alkylenamines. However, such processes are still inadequate from the industrial point of view. Particularly it is desired to develop a process for producing high quality alkylenamines having high non-cyclic rates by using a solid catalyst having high catalytic activities and high heat resistance and being hardly soluble in the reaction solution, for the production of alkylenamines using alkanolamines as starting material.

Under these circumstances, the present inventors have conducted extensive researches on a process for producing alkylenamines having alkylene chains increased over ammonia and/or alkylenamines as starting material by the reaction of the ammonia and/or alkylenamines with alkanolamines. As a result, they have found that niobium oxide treated with an acid has high activities as catalyst and is a solid hardly soluble in a reaction solution containing water, and it is also excellent in the heat resistance. The present invention has been accomplished on the basis of these discoveries.

The present invention provides a process for producing an alkylenamine, which comprises reacting ammonia and/or an alkylenamine with an alkanolamine in the presence of niobium oxide treated with an acid, to obtain an alkylenamine having an increased number of alkylene chains over the ammonia and/or the alkylenamine as starting material.

Now, the present invention will be described in further detail.

The catalyst used in the present invention is a catalyst comprising a mixture of niobium oxide and an inorganic acid. The catalyst comprising a mixture of niobium oxide and an inorganic acid is obtained by treating niobium oxide with an inorganic acid. As the acid to be contacted to niobium oxide, an inorganic acid such as nitric acid, hydrochloric acid, hydrofluoric acid, boric acid, phosphoric acid or sulfuric acid is preferred. Boric acid, phosphoric acid and sulfuric acid are particularly preferred from the viewpoint of the activities, the selectivity and the heat resistance. There is no particular restriction as to the concentration of the boric acid solution. However, the concentration is usually at least 0.01M and at most 4.4M, preferably at least 0.1M and less than 3M. If the boric acid concentration exceeds the above range, there will be an adverse effect such that the large amount of boric acid acts as catalyst to increase cyclic products in the resulting amine, whereby the quality of the amine will be low. If the boric acid concentration is lower than the above range, the heat resistance of the catalyst tends to be low. Namely, the catalyst tends to transform to crystals having a small surface area at a low temperature. Further, there will be an increase of cyclic products in the resulting amine. There is no particular restriction as to the concentration of a aqueous phosphoric acid solution. However, the concentration is usually from 0.01 to 10M, preferably from 0.1 to 5M. If the phosphoric acid concentration exceeds this range, the surface area of the catalyst decreases substantially, and phosphoric acid tends to elute into the reaction solution containing water. Further, there will be an adverse effect such that a large amount of phosphoric acid or its salt acts as catalyst to increase cyclic products in the resulting amine, whereby the quality of the resulting amine tends to be low. If the phosphoric acid concentration is lower than the above range, the heat resistance of the catalyst tends to be low, and cyclic products in the resulting amine tend to increase. Sulfuric acid may be used at a concentration of from 0.001 to 18M. Particularly preferred as the concentration of sulfuric acid is at least 0.01M. If the sulfuric acid concentration is lower than 0.001M, the effects obtained by the treatment with sulfuric acid tend to be small, and the activities of the catalyst tend to be low.

A small amount of boric acid or phosphoric acid remains in the niobium oxide used in the process of the present invention. In the case of boric acid, the amount is usually from 0.01 to 5 mols, preferably at least 0.01 mol and less than 2 mols, per mol of niobium oxide. Likewise, in the case of phosphoric acid, the amount is usually at least 0.01 mol and less than 1 mol, preferably at least 0.01 mol and less than 0.75 mol, per mol of niobium oxide. If the remaining amount is less than 0.01 mol, the heat resistance of the catalyst tends to be low. Namely, the catalyst tends to transform to crystals having a small surface area at a low temperature. Further, cyclic products in the resulting amine tend to increase. On the other hand, if the amount of boric acid exceeds 5 mols, boric acid acts as catalyst, and the amount of cyclic products in the resulting amine tends to increase, whereby the quality tends to be low. If the amount of phosphoric acid is 1 mol or higher, the surface area of the catalyst tends to decrease substantially, and phosphoric acid tends to elute into the reaction solution containing water. Further, since phosphoric acid or its salt acts as catalyst, the amount of cyclic products in the resulting amine tends to increase, whereby the quality tends to be low. If sulfuric acid remains, the amount of sulfuric acid is preferably at most 5 mols, more preferably at most 1 mol, per mol of niobium oxide. If sulfuric acid remains in an amount exceeding the above range, the large amount of sulfuric acid acts as catalyst, and presents an adverse effect such as an increase of cyclic products in the resulting amine, whereby the quality of the formed amine tends to be low.

Niobium oxide used in the process of the present invention includes niobium pentoxide, niobium tetroxide, niobium trioxide, niobium dioxide and niobium monoixde. Any niobium oxide may be used. However, it is preferred to use niobium pentoxide. There is no particular restriction as to the form of niobium pentoxide. It may be used in the form of its hydrate or anhydride. Niobium pentoxide in the form of hydrate is referred to also as niobic acid, and it is usually represented by the formula $Nb_2O_5 \cdot xH_2O$ ($0 < X \leq 5$). When $x=5$, it may be called niobium hydroxide.

There is no particular restriction as to the manner for the preparation of niobium oxide to be used in the process of the present invention. For example, a method may be used wherein niobium pentoxide is impregnated with an aqueous boric acid solution, an aqueous phosphoric acid solution having a low concentration or an aqueous sulfuric acid solution, followed by evaporation to dryness and calcining. Washing with water may or may not be conducted. However, in a case where a large amount of an acid is present, it is preferred to conduct washing with water.

The catalyst to be used in the process of the present invention, may or may not be calcined before use. When calcination is conducted, there is no particular restriction as to the temperature for calcination. However, when treated with boric acid, it is calcined preferably at a temperature of at most 600° C. When treated with phosphoric acid, it is calcined preferably at a temperature of at most 700° C. Likewise, when treated with sulfuric acid, it is calcined preferably at a temperature of at most 500° C. If the calcination is conducted at a temperature exceeding the above-mentioned ranges, crystallization of the catalyst tends to take place, whereby the surface area tends to be small, and the catalytic activities tend to be low.

In the present invention, there is no particular restriction as to the shape of the catalyst. Depending upon the reaction system, it may be used as powder, or may be used in a molded form. For example, in a suspended bed system, it is used in a powder or granular form. In a fixed bed system, it is used in a molded form of pellets or beads.

The molding method of the catalyst includes extrusion molding, tablet molding or granule molding. For the molding, silica, alumina, alumina silica, clay or the like may be added as a binder.

Further, in order to increase the surface area of the catalyst, the niobium oxide treated with acid may be supported on a carrier such as silica, alumina, titania, zirconia or porous vycor glass.

The amount of the niobium oxide treated with an acid used as catalyst in the present invention may be at any level so long as it is sufficient to have the reaction proceeded at an industrially useful reaction rate.

Ammonia or the alkylenamine to be used in the process of the present invention is a compound represented by the formula:

wherein a is a number of from 2 to 6, r is a number of from 0 to 6, $R_1$ is hydrogen or an alkyl group having from 1 to 4 carbon atoms, $R_1'$ is a group represented by the formula (1):

wherein b is a number of from 2 to 6, d is 0 or 1, and s is a number of from 0 to 4, or a compound represented by the formula II:

wherein e is a number of from 2 to 6, f is a number of from 2 to 6, and each of $R_2$ and $R_2'$ is a group represented by the formula (2):

$$-[(CH_2)_g NH]_f-H \qquad (2)$$

wherein g is a number of from 2 to 6, and t is a number of 0 to 5.

Either the compound of the formula I or the compound of the formula II may be employed. Preferably, however, ammonia or an alkylenamine of the formula I is employed. When an alkylenamine of the formula I is used, a high quality alkylenamine having a high non-cyclic rate is obtainable. Ammonia and the alkylenamine of the formula I include ammonia, ethylenamines such as ethylenediamine, diethylenetriamine, triethylenetetramine, tetraethylenepentamine, pentaethylenehexamine and hexaethyleneheptamine, propyleneamines such as propylenediamine and dipropylenetriamine, butyleneamines such as butylenediamine and dibutylenetriamine, alkylenamines such as hexamethylenediamine and alkylated products thereof such a N-methylethylenediamine and N-ethylethylenediamine. Among them, ethylenamines such as ethylenediamine and diethylenetriamine are preferred as starting material to be used in the process of the present invention.

Ammonia and alkylenamines to be used in the process of the present invention may be used alone or in combination as a mixture of two or more different kinds.

The alkanolamine to be used in the process of the present invention is a compound represented by the formula III:

$$H_2N-[(CH)_h N]_u-(CH)_h-OH \qquad (III)$$
$$\phantom{H_2N-[(}|\phantom{CH)_h N]_u-(}|\phantom{CH)_h-}|$$
$$\phantom{H_2N-[(CH}R_3\phantom{)_h }R_3'\phantom{ ]_u-(}R_3$$

wherein h is a number of from 2 to 6, u is a number of from 0 to 5, $R_3$ is hydrogen or an alkyl group having from 1 to 4 carbon atoms, and $R_3'$ is a group represented by the formula (3):

$$-[(CH_2)_i-(NH)_j]_v-H \qquad (3)$$

wherein i is a number of from 1 to 6, j is 0 or 1, and v is a number of from 0 to 4, or a compound represented by the formula IV:

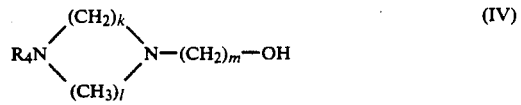

wherein k is a number of from 2 to 6, l is a number of from 2 to 6, m is a number of from 2 to 6, and $R_4$ is a group represented by the formula (4):

$$-[(CH_2)_n-NH]_w-H \qquad (4)$$

Wherein n is a number of from 2 to 6, and w is a number of from 0 to 5.

Either the compound of the formula III or the compound of the formula IV may be employed. However, the alkanolamine of the formula III is preferably employed. When the alkanolamine of the formula III is used, a high quality alkylenamine having a high non cyclic rate is obtainable. The alkanolamine of the formula III includes alkanolamines such as monoethanolamine, N-(2-aminoethyl)ethanolamine, monopropanolamine and N-(3-aminopropyl)propanolamine. As the starting material to be used in the process of the present invention, ethanolamines such as monoethanolamine and N-(2-aminoethyl)ethanolamine are preferred.

The alkanolamines to be used in the process of the present invention may be used alone or in combination as a mixture of two or more different kinds.

The combination of starting materials supplied for the reaction in the process of the present invention includes the following three types:
1) Ammonia and an alkanolamine;
2) An alkylenamine and an alkanolamine; and
3) Ammonia, an alkylenamine and an alkanolamine.
The reaction may be conducted any one of such combinations.

Preferred combinations of starting materials include:
1) Ammonia and an alkanolamine of the formula III;
2) An alkylenamine of the formula I other than ammonia and an alkanolamine of the formula III; and
3) Ammonia and an alkylenamine of the formula I and an alkanolamine of the formula III.

More preferred combinations of starting materials include:
1) Ammonia and an ethanolamine;
2) An ethylenamine and an ethanolamine; and
3) Ammonia, an ethylenamine and an ethanolamine.

Preferred molar ratios of the starting materials to be supplied in the process of the present invention are as follows:
1) In the case where ammonia and an alkanolamine are used as starting materials, the molar ratio of ammonia/the alkanolamine is from 2 to 30;
2) In a case where an alkylenamine and an alkanolamine are used as starting materials, the molar ratio of the alkylenamine/the alkanolamine is from 0.5 to 10; and
3) In a case where ammonia, an alkylenamine and an alkanolamine are used as starting materials, the molar ratio of (ammonia+the alkylenamine)/the alkanolamine is from 0.5 to 30.

In each case, the quality of the resulting alkylenamine varies depending upon the molar ratio of the starting materials. If the molar ratio is smaller than the above-mentioned ranges, piperazine ring-containing amines will be produced in a substantial amount, whereby alkylenamines having undesirable quality tend to form. If the molar ratio is larger than the above ranges, the reaction rate tends to decrease, and the pressure is required to be extremely high, such being not practical.

In the process of the present invention, the resulting alkylenamine differs depending upon the types of the starting materials. When an alkanolamine is reacted to ammonia and/or an alkylenamine, the resulting alkylenamine has alkylene chains increased over the ammonia or the alkylenamine as starting material. Namely, when the alkanolamine of the formula III is reacted to the ammonia and/or the alkylenamine of the formula I, the resulting alkylenamine will be a compound represented by the formula V:

$$H_2N-[(CH)_o N]_x-H \qquad (V)$$
$$\phantom{H_2N-[(C}|\phantom{H)_o N]_x-}|$$
$$\phantom{H_2N-[(CH}R_5\phantom{)_o }R_5'$$

wherein o is a number of from 2 to 6, x is a number of 1 to 7, $R_5$ is hydrogen or an alkyl group having from 1 to 4 carbon atoms, and $R_5'$ is a group of the formula (5):

$$-[(CH_2)_p-(NH)_q]_y-H \qquad (5)$$

wherein p is a number of from 1 to 6, q is 0 or 1, and y is a number of 0 to 4, wherein x and/or y in the resulting alkylenamine is a number larger at least by one than r and/or s of the ammonia or the alkylenamine as starting material. Thus, an alkylenamine having an increased number of alkylene chains over the starting material is obtainable. For example, when ammonia is reacted with monoethanolamine, ethylenediamine and noncyclic polyethylenepolyamines such as diethylenetriamine, triethylenetetramine, tetraethylenepentamine and pentaethylenehexamine will be formed. When ethylenediamine is reacted with monoethanolamine, the above-mentioned non-cyclic polyethylenepolyamines will be formed. When ammonia and ethylenediamine are reacted with monoethanolamine, ethylenediamine and the above-mentioned non-cyclic polyethylenepolyamines will be formed.

In the process of the present invention, the reaction is conducted usually at a temperature within a range of from 200° to 400° C., preferably from 240° to 350° C. If the temperature is less than 200° C., the reaction rate tends to be substantially low, and if it exceeds 400° C., the resulting alkylenamine tends to undergo decomposition, such being not practical.

In the process of the present invention, the reaction may be conducted in a gas phase or in a liquid phase. However, it is preferred to conduct it in a liquid phase in order to produce a high quality alkylenamine.

In the process of the present invention, the reaction may be conducted by a suspended batch, semi-batch or continuous system, or by a fixed bed system. However, the fixed bed system is industrially advantageous from the viewpoint of the operation, apparatus and economy.

In the process of the present invention, the pressure for the reaction varies substantially depending upon whether the reaction is a gas phase reaction or a liquid phase reaction, or whether or not ammonia is used. Therefore, it is difficult to define the pressure range. However, for example, in the case of a liquid phase reaction using no ammonia, the pressure is within a range of from about 1 to about 300 kg/cm$^2$G.

In the process of the present invention, the catalyst will usually be separated and recovered from the reaction solution, and then the starting material will be separated and recovered by distillation. The separated and recovered starting material will be recycled to the reaction zone, as the case requires. A part of the reaction product may be recycled to the reaction zone in order to change the composition of the reaction product. The separation of the starting material and the product is usually conducted by distillation. Such distillation may be conducted by a continuous system or by a batch system.

The reaction product may be treated with active carbon or sodium borohydride in order to improve the purity of color tone of the reaction product. The color tone, odor, etc. of the reaction product may be improved by conducting the reaction in the presence of hydrogen.

The formed water may be removed from the reaction zone in order to reduce the formation of amines undesirable from the viewpoint of quality such as hydroxyl group-containing amines or to improve the reaction rate. Otherwise, the reaction may be conducted with an additional of water in order to prolong the catalytically useful life or to make it easy to handle ammonia or the alkylenamine.

In the present invention, niobium oxide is treated with an acid, whereby it is possible to obtain niobium oxide which is catalytically highly active, resistant to corrosion by the reaction solution and excellent in the heat resistance. The present invention provides a process for producing a high quality alkylenamine in good yield by using such niobium oxide as catalyst, and thus it is industrially extremely valuable.

Now, the present invention will be described in further detail with reference to Examples. However, it should be understood that the present invention is by no means restricted to such specific Examples.

Alkylenamines as reaction products and alkylenamines and alkanolamines as starting materials will be represented by the following abbreviations:
EDA: Ethylenediamine
MEA: Monoethanolamine
PIP: Piperazine
AEP: N-(2-aminoethyl)piperazine
DETA: Diethylenetriamine
AEEA: N-(2-aminoethyl)ethanolamine
TETA: Triethylenetetramine (linear, branched, cyclic or hydroxyl group-containing isomer)
TEPA Tetraethylenepentamine (linear, branched, cyclic or hydroxyl group-containing isomer)
PEHA: Pentaethylenehexamine (linear, branched, cyclic or hydroxyl group-containing isomer)
NH$_3$: Ammonia EXAMPLE 1: Preparation of catalysts

CATALYST A 5 g of niobium oxide (manufactured by CBMM Co.) was added to 10 ml of a 1M boric acid aqueous solution and impregnated for 24 hours. Then, it was evaporated to dryness at 120° C. and further calcined at 400° C. for 2 hours under a dry air stream to obtain Catalyst A. As a result of the elemental analysis, the molar ratio of boric acid/niobium oxide was 1.20. From the differential thermal analysis, the transition temperature of catalyst A for crystallization from the amorphous state was found to be 590° C.

CATALYST B 5 g of niobium oxide (manufactured by CBMM Co.) was added to 10 ml of 2M boric acid/ethanol and impregnated for 24 hours. It was then washed with water, evaporated to dryness at 80° C. and further calcined at 400° C. for 2 hours under a dry air stream to obtain Catalyst B. As a result of the elemental analysis, the molar ratio of boric acid/niobium oxide was 0.92.

CATALYST C 5 g of niobium oxide (manufactured by CBMM Co.) was added to 10 ml of 5M phosphoric acid and impregnated for 24 hours. It was then evaporated to dryness at 120° C. and further calcined at 600° C. for 2 hours under a dry air stream to obtain Catalyst C. As a result of the elemental analysis, the molar ratio of phosphoric acid/niobium oxide was 0.71, and the BET specific surface area was 9.1 m$^2$/g. From the X-ray diffraction pattern, no phosphate of niobium was observed.

CATALYST D

Catalyst D was prepared in the same manner as in the preparation of Catalyst C except that the concentration of phosphoric acid was changed to 2M. As a result of the elemental analysis, the molar ratio of phosphoric acid/niobium oxide was 0.30, and the BET specific surface area was 45.2 m²/g. From the X-ray diffraction pattern, no phosphate of niobium was observed.

CATALYST E 5 g of niobium oxide (manufactured by CBMM Co.) was added to 10 ml of 1M phosphoric acid and impregnated for 24 hours. It was then evaporated to dryness at 120° C. and further calcined at 400° C. for 2 hours under a dry air stream to obtain Catalyst E. As a result of the elemental analysis, the molar ratio of phosphoric acid/niobium oxide was 0.12. The BET specific surface are of Catalyst E was 57.8 m²/g. From the X-ray diffraction pattern, it was found to be amorphous.

CATALYST F

Catalyst E was calcined at 600° C. for 2 hours under a dry air stream to obtain Catalyst F. As a result of the elemental analysis, the molar ratio of phosphoric acid/niobium oxide was 0.12. The BET specific surface area of Catalyst F was 43.9 m²/g. From the X-ray diffraction pattern, no phosphate of niobium was observed.

CATALYST G

Catalyst G was prepared in the same manner as in the preparation of Catalyst C except that the concentration of phosphoric acid was changed to 0.5M. As a result of the elemental analysis, the molar ratio of phosphoric acid/niobium oxide was 0.07, and the BET specific surface area was 44.4 m²/g. From the X-ray diffraction pattern, no phosphate of niobium was observed.

CATALYST H

Catalyst H was prepared in the same manner as in the preparation of Catalyst C except that the concentration of phosphoric acid was changed to 0.2M. As a result of the elemental analysis, the molar ratio of phosphoric acid/niobium oxide was 0.02, and the BET specific surface area was 51.7 m²/g. From the X-ray diffraction pattern, no phosphate of niobium was observed.

To 1 g of this Catalyst H, 100 ml of distilled water was added, and the mixture was refluxed for one hour. The catalyst was collected by filtration and calcined at 600° C. for 2 hours under a dry air stream, whereby the catalyst was recovered 100%.

CATALYST I 5 g of niobium oxide (manufactured by CBMM Co.) was added to 10 ml of a 1M sulfuric acid aqueous solution and impregnated for 24 hours. It was then evaporated to dryness and further calcined at 400° C. for 2 hours under a dry air stream to obtain Catalyst I. To this catalyst, 100 ml of distilled water was added, and the mixture was refluxed for one hour. The catalyst was collected by filtration and calcined at 400° C. for 2 hours under a dry air stream, whereby the catalyst was recovered 100%.

CATALYST J

Catalyst J was prepared in the same manner as in the preparation of Catalyst A except that a 0.1M sulfuric acid aqueous solution was used.

CATALYST K 5 g of niobium oxide (manufactured by CBMM Co.) was dissolved in 30 ml of 18M sulfuric acid at 150° C. The solution was cooled, and then water was added. Formed precipitates were collected by filtration, washed with water and calcined at 400° C. for 2 hours under a dry air stream to obtain Catalyst K.

COMPARATIVE CATALYST A 5 g of niobium oxide (manufactured by CBMM Co.) was calcined at 400° C. for 2 hours under a dry air stream to obtain Comparative Catalyst A. The BET specific surface area of Comparative Catalyst A was 99 m²/g. From the differential thermal analysis, the transition temperature of Comparative Catalyst A for crystallization from the amorphous state was found to be 563° C.

COMPARATIVE CATALYST B 130 g (0.30 mol) of lanthanum nitrate hexahydrate was dissolved in deionized water under stirring. Separately, 79.2 g (0.60 mol) of diammonium hydrogen phosphate was dissolved in deionized water under stirring. While vigorously stirring the aqueous diammonium hydrogen phosphate solution, the aqueous lanthanum nitrate solution was added at once, whereby thick bulky precipitates formed. A thick creamy suspension was obtained by stirring, and the precipitates were collected by filtration under suction. The paste-like solid thus obtained was thoroughly washed with deionized water and then dried at a temperature of from 80° to 90° C. to obtain an acidic lanthanum phosphate, which is designated as Comparative Catalyst B.

COMPARATIVE CATALYST C 5 g of niobium oxide (manufactured by CBMM Co.) was added to 20 ml of 17M phosphoric acid and impregnated for 24 hours. It was then evaporated to dryness at 120° C. and further calcined at 600° C. for 2 hours under a dry air stream to obtain Comparative Catalyst C. As a result of the elemental analysis, the molar ratio of phosphoric acid/niobium oxide was 6.1. The BET specific surface area of Comparative Catalyst C was 1 m²/g. From the X-ray diffration pattern, it was found that niobium phosphate formed.

To 1 g of this catalyst, 100 ml of distilled water was added, and the mixture was refluxed for one hour. Then, the catalyst was collected by filtration and calcined at 600° C. for 2 hours under a dry air stream, whereby 0.38 g of the catalyst was recovered.

COMPARATIVE CATALYST D

Comparative Catalyst D was prepared in the same manner as in the Preparation of Comparative Catalyst C except that 12M phosphoric acid was used in an amount of 10 ml. As a result of the elemental analysis, the molar ratio of phosphoric acid/niobium oxide was 1.22. The BET specific surface area was 1 m²/g. From the X-ray diffration pattern, no phosphate of niobium was observed.

COMPARATIVE CATALYST E 5 g of niobium oxide (manufactured by CBMM Co.) was calcined at 600° C. for 2 hours under a dry air stream to obtain Comparative Catalyst E. The BET specific surface area of Comparative Catalyst E was 12 m²/g.

EXAMPLE 2

Into a 200 ml autoclave equipped with an electromagnetic stirrer, 60 g of EDA, 30 g of MEA and 1 g of Catalyst A were charged. After flushing with nitrogen, the autoclave was heated to 300° C. and maintained at that temperature for 5 hours. The reaction pressure was 42 kg/cm$^2$G. After cooling, the reaction solution was withdrawn and analyzed by gas chromatography. As a result of the analysis, the conversion of MEA was 54.8%, and the composition of the reaction solution excluding the starting materials and formed water was as follows: PIP: 2.58% by weight, DETA: 43.93% by weight, AEEA: 0.07% by weight, AEP: 1.36% by weight, TETA: 12.48% by weight, and TEPA: 0.01% by weight. The non-cyclic rate of formed TETA [gas chromatogram area %: (branched+linear)/(branched+linear+cyclic+hydroxyl group-containing)×100] was 95.36%.

COMPARATIVE EXAMPLE 1

The reaction was conducted under the same condition as in Example 2 except that 1 g of Comparative Catalyst A was used as catalyst. The reaction pressure was 40 kg/cm$^2$G. As a result of the analysis of the reaction solution, the conversion of MEA was 47.1%, and the composition of the reaction product excluding the starting materials and formed water was as follows: PIP: 2.37% by weight, DETA: 47.61% by weight, AEEA: 0.16% by weight, AEP: 1.23% by weight, TETA: 11.23% by weight, and TEPA: 0.74% by weight. The non-cyclic rate of TETA was 93.06%.

COMPARATIVE EXAMPLE 2

The reaction was conducted under the same condition as in Example 2 except that 3 g of boric acid was used as catalyst. As a result of the analysis of the reaction solution, the conversion of MEA was 41.0%, and the composition of the reaction product excluding the starting materials and formed water was as follows: PIP: 3.12% by weight, DETA: 58.72% by weight, AEEA: 5.02% by weight, AEP: 1.28% by weight, TETA: 10.84% by weight, and TEPA: 0.21% by weight. The non-cyclic rate of TETA was 5.23%.

COMPARATIVE EXAMPLE 3

The reaction was conducted under the same condition as in Example 2 except that 3 g of crystallized niobium oxide made by Soekawa Kagaku K. K. was used as catalyst. As a result of the analysis of the reaction solution, the conversion of MEA was 10.1%, and the composition of the reaction product excluding the starting materials and formed water was as follows: PIP: 5.68% by weight, DETA: 7.20% by weight, and AEP: 0.97% by weight.

COMPARATIVE EXAMPLE 4

The reaction was conducted under the same condition as in Example 2 except that 1 g of Comparative Catalyst B was used. As a result of the analysis of the reaction solution, the conversion of MEA was 26.8%, and the composition of the reaction product excluding the starting materials and formed water was as follows: PIP: 4.22% by weight, DETA: 55.72% by weight, AEEA: 17.02% by weight, AEP: 0.98% by weight, TETA: 5.54% by weight, and TEPA: 0.38% by weight.

EXAMPLE 3

Into a 200 ml stainless steel autoclave equipped with an electromagnetic stirrer, 30 g of EDA, 15 g of MEA and 3 g of Catalyst B were charged. After flushing with nitrogen, 25.4 g of NH$_3$ was added thereto, and the autoclave was heated to 280° C. and maintained at that temperature for 30 minutes. The reaction pressure was 80 kg/cm$^2$G. After cooling, the reaction solution was withdrawn and analyzed by gas chromatography. As a result of the analysis, the conversion of MEA was 59.8%, and the composition of the reaction product excluding the starting materials and formed water was as follows: PIP: 2.73% by weight, DETA: 46.05% by weight, AEEA: 3.01% by weight, AEP: 2.05% by weight, TETA: 13.98% by weight, TEPA: 4.12% by weight, and PEHA: 1.09% by weight.

EXAMPLE 4

The reaction was conducted under the same condition as in Example 2 except that Catalyst C was used as catalyst. The reaction pressure was 36.0 kg/cm$^2$G. After cooling, the reaction solution was withdrawn and analyzed by gas chromatography. As a result of the analysis, the conversion of MEA was 51.5%, and the composition of the reaction product excluding the starting materials and formed water was as follows: PIP: 1.99% by weight, DETA: 58.87% by weight, AEEA: 3.34% by weight, AEP: 1.38% by weight, TETA: 12.73% by weight, and TEPA: 2.06% by weight. The PIP/DETA ratio representing the cyclic rate of the formed ethylenamine was 0.034.

COMPARATIVE EXAMPLE 5

The reaction was conducted under the same condition as in Example 2 except that 0.3 g of phosphoric acid was used as catalyst, and the reaction time was changed to 4.5 hours. The reaction pressure was 76.5 kg/cm$^2$G. As a result of the analysis of the reaction solution, the conversion of MEA was 49.4%, and the composition of the reaction product excluding the starting materials and formed water was as follows: PIP: 4.04% by weight, DETA: 42.57% by weight, AEEA: 2.09% by weight, AEP: 1.35% by weight, TETA: 7.38% by weight, TEPA: 1.17% by weight, and PEHA: 0.18% by weight. The PIP/DETA ratio was 0.095.

EXAMPLES 5 to 9

The reaction was conducted under the same condition as in Example 2 except that the catalyst as identified in Table 1 was used in an amount of 1 g. The results are shown in Table 1. The TETA cyclic ratio is a numerical value showing the ratio of cyclic products and is represented by the gas chromatogram area % of the cyclic isomers among TETA isomers i.e. [cyclic isomer/(branched+linear+hydroxyl group-containing+cyclic isomer)×100].

COMPARATIVE EXAMPLES 6 to 8

The reaction was conducted under the same condition as in Example 2 except that the catalyst as identified in Table 1 was used in an amount of 1 g. The results are shown in Table 1.

TABLE 1

| | Catalyst | Conversion of MEA (%) | Cyclic ratio of TETA (%) |
|---|---|---|---|
| Example 5 | Catalyst D | 39.3 | 2.21 |
| Example 6 | Catalyst E | 52.1 | 2.70 |
| Example 7 | Catalyst F | 44.9 | 2.35 |
| Example 8 | Catalyst G | 42.2 | 2.35 |
| Example 9 | Catalyst H | 21.7 | 2.19 |
| Comparative Example 6 | Comparative Catalyst C | 64.4 | 11.22 |
| Comparative | Comparative | 48.3 | 4.53 |

TABLE 1-continued

| Catalyst | | Conversion of MEA (%) | Cyclic ratio of TETA (%) |
|---|---|---|---|
| Example 7 Comparative Example 8 | Catalyst D Comparative Catalyst E | 10.1 | No formation of TETA |

EXAMPLES 10 to 12

Into a 200 ml stainless steel autoclave equipped with an electromagnetic stirrer, 3 g of Catalyst D and starting materials as identified in Table 2 in the amounts as identified in Table 2 were charged. After flushing with nitrogen, the mixture was reacted at 300° C. for one hour. The results are shown in Table 2.

TABLE 2

| | Starting materials (g) | | Conversion of MEA (%) | Composition of reaction product (wt % excluding formed water and starting materials) | | | | | |
|---|---|---|---|---|---|---|---|---|---|
| | EDA | MEA | | PIP | DETA | AEEA | AEP | TETA | TEPA | PEHA |
| Example 10 | 30 | 60 | 41.5 | 3.7 | 23.8 | 20.8 | 2.7 | 14.8 | 3.6 | 0.7 |
| Example 11 | 45 | 45 | 41.9 | 3.0 | 47.3 | 8.8 | 1.9 | 16.7 | 3.6 | 0.3 |
| Example 12 | 60 | 30 | 42.2 | 2.4 | 62.7 | 1.9 | 1.1 | 13.3 | 0.5 | 0.0 |

EXAMPLE 13

Into a 200 ml stainless steel autoclave equipped with an electromagnetic stirrer, 3 g of Catalyst D, 60 g of EDA and 30 g of MEA were charged. After flushing with nitrogen, NH$_3$ was introduced in an amount of 34.5 g. The mixture was reacted at 280° C. for 5 hours. The reaction pressure was 221 kg/cm$^2$G. The reaction solution was analyzed by gas chromatography. The conversion of MEA was 43.7%. The composition of the reaction solution was as follows: Water: 4.7% by weight, EDA: 56.9% by weight, PIP: 0.6% by weight, DETA: 11.9% by weight, AEEA: 0.6% by weight, AEP: 0.3% by weight, and TETA: 1.5% by weight.

EXAMPLE 14

The reaction was conducted under the same condition as in Example 2 except that Catalyst I was used as catalyst. The reaction pressure was 39 kg/cm$^2$G. After cooling, the reaction solution was withdrawn and analyzed by gas chromatography. As a result of the analysis, the conversion of MEA was 64.4%, and the composition of the reaction product excluding the starting materials and formed water was as follows: PIP: 2.56% by weight, DETA: 40.74% by weight, AEEA: 1.56% by weight, AEP: 1.94% by weight, TETA: 16.49% by weight, and TEPA: 1.28% by weight.

EXAMPLE 15

Into a 200 ml stainless steel autoclave equipped with an electromagnetic stirrer, 30 g of EDA, 60 g of MEA and 3 g of Catalyst J were charged. After flushing with nitrogen, the autoclave was heated to 300° C. and maintained at that temperature for one hour. The reaction pressure was 33 kg/cm$^2$G. After cooling, the reaction solution was withdrawn and analyzed by gas chromatography. As a result of the analysis, the conversion of MEA was 40.2%, and the composition of the reaction product excluding the starting materials and formed water was as follows: PIP: 3.63% by weight, DETA: 23.54% by weight, AEEA: 20.95% by weight, AEP: 2.70% by weight, TETA: 14.77% by weight, TEPA: 3.59% by weight, and PEHA: 0.67% by weight. The non-cyclic ratio of formed TETA [gas chromatogram area %: (branched+linear)/(branched+linear+cyclic+hydroxy group-containing(×100] was 67.6%.

COMPARATIVE EXAMPLE 9

The reaction was conducted under the same condition as in Example 15 except that 0.93 g of sulfuric acid was used as catalyst, and the reaction time was changed to 2 hours and 25 minutes. The reaction pressure was 35 kg/cm$^2$G. As a result of the analysis of the reaction solution, the conversion of MEA was 35.5%, and the composition of the reaction product excluding the starting materials and formed water was as follows: PIP: 1.99% by weight, DETA: 16.77% by weight, AEEA: 19.29% by weight, AEP: 1.43% by weight, TETA: 7.26% by weight, TEPA: 1.59% by weight, and PEHA: 0.13% by weight. The non-cyclic ratio of formed TETA was 64.76%.

EXAMPLE 16

Into a 200 ml stainless steel autoclave equipped with an electromagnetic stirrer, 30 g of EDA, 15 g of MEA and 3 g of Catalyst K were charged. After flushing with nitrogen, the NH$_3$ was added in an amount of 25.7 g, and the mixture was reacted at 280° C. for one hour. The reaction pressure was 78 kg/cm$^2$G. After cooling, the reaction solution wa withdrawn and analyzed by gas chromatography. As a result of the analysis, the conversion of MEA was 33.9%, and the composition of the reaction product excluding the starting materials and formed water was as follows: PIP: 1.70% by weight, DETA: 48.69% by weight, AEEA: 7.73% by weight, AEP: 0.72% by weight, TETA: 8.72% by weight, and TEPA: 0.32% by weight.

What is claimed is:

1. A process for producing an alkylenamine, which process consists essentially of reacting ammonia and/or an alkylenamine with an alkanolamine in the presence of a catalyst comprising a mixture of niobium oxide and an inorganic acid, to obtain an alkylenamine having an increased number of alkylene chains over the ammonia and/or the alkylenamine as starting material.

2. The process according to claim 1, wherein the acid is boric acid, phosphoric acid or sulfuric acid.

3. The process according to claim 1, wherein the alkylenamine as starting material is an ethylenamine.

4. The process according to claim 1, wherein the alkanolamine is an ethanolamine.

* * * * *